United States Patent [19]

Detz et al.

[11] 4,347,394

[45] Aug. 31, 1982

[54] BENZENE SYNTHESIS

[75] Inventors: Clifford M. Detz, San Rafael; Leslie A. Field, Oakland, both of Calif.

[73] Assignee: Chevron Research Company, San Francisco, Calif.

[21] Appl. No.: 215,194

[22] Filed: Dec. 10, 1980

[51] Int. Cl.$^3$ .................... C07C 2/52; C07C 12/46; C07C 15/02
[52] U.S. Cl. ..................... 585/419; 585/417
[58] Field of Search ................. 585/419, 417

[56] References Cited

U.S. PATENT DOCUMENTS

| | | | |
|---|---|---|---|
| 3,756,942 | 9/1973 | Cattanach | 208/137 |
| 3,760,024 | 9/1973 | Cattanach | 260/673 |
| 3,813,330 | 5/1974 | Givens et al. | 208/66 |
| 3,819,507 | 6/1974 | Oishi | 585/417 |
| 3,827,968 | 8/1974 | Givens et al. | 208/49 |
| 4,104,320 | 8/1978 | Bernard et al. | 585/419 |
| 4,120,910 | 10/1978 | Chu | 585/417 |
| 4,157,293 | 6/1979 | Plank et al. | 585/417 X |
| 4,210,603 | 7/1980 | Cihonski | 585/419 X |
| 4,260,839 | 4/1981 | Chen et al. | 585/417 X |

Primary Examiner—Paul F. Shaver
Attorney, Agent, or Firm—D. A. Newell; S. R. La Paglia; W. L. Stumpf

[57] ABSTRACT

A process for selectively producing benzene using intermediate pore size zeolites substantially free of acidity is disclosed.

13 Claims, No Drawings 4,347,394

BENZENE SYNTHESIS

TECHNICAL FIELD

Benzene is one of the basic raw materials of the chemical industry. It is used to synthesize rubbers, dyes, and detergents and is also used as a solvent and as an octane increasing gasoline additive. Benzene is usually produced from hydrocarbonaceous feed materials in a mixture with toluene, the xylenes, and higher aromatics through reforming reactions such as cyclization, dehydrogenation, and isomerization. A typical reforming process uses straight-run naphtha feeds and platinum-containing catalysts.

Recovery of purified benzene from the benzene-toluene-xylene mixture requires some further treatment, for example some combination of fractionation, solvent extraction, and adsorptive extraction. The efficiency of these separation steps increases as the benzene content of the reformate increases. However, there has been no particularly efficient process for producing a high-benzene reformate which need not be fractionally distilled, solvent extracted, or dealkylated to obtain a high benzene content feed suitable for subsequent purification steps.

The object of the present invention is to provide such a process.

We have discovered that intermediate pore size zeolites can be used to convert light straight-run naphthas (and similar mixtures) to highly aromatic mixtures. Most surprisingly and unlike the product of traditional reforming processes, the primary constituent of these aromatic mixtures is benzene. Benzene synthesis using our process becomes very much more efficient than processes known to the art. The importance of this development can scarcely be overestimated in view of the increasing demands for benzene by the chemical and the automotive industries, and in view of the decreasing amounts of petroleum feeds available to the world market.

BACKGROUND ART

A number U.S. patents which relate to the production of benzene/toluene/xylene (BTX) mixtures from various feeds have issued.

U.S. Pat. No. 3,756,942, Cattanach, Sept. 4, 1973 discloses the preparation of BTX from a $C_5$ to 250° F. feed using ZSM-5.

U.S. Pat. No. 3,760,024, Cattanach, Sept. 18, 1973 discloses the preparation of $C_6{}^+$ aromatics from $C_2$ to $C_4$ paraffins or olefins using ZSM-5.

U.S. Pat. No. 3,775,501, Kaeding, Nov. 27, 1973 discloses BTX preparation from olefins using ZSM-5 in the presence of oxygen.

U.S. Pat. No. 3,813,330, Givens, May 28, 1974 discloses aromatizing olefins in the presence of easily cracked paraffins to produce BTX using ZSM-5.

U.S. Pat. No. 3,827,968, Givens, Aug. 6, 1974 discloses a two step process for preparing BTX from olefins using ZSM-5. $C_2$-$C_5$ olefins are oligomerized to $C_5$-$C_9$ olefins which are then aromatized.

U.S. Pat. No. 3,843,740, Mitchell, Oct. 22, 1974 discloses the preparation of BTX using a two step process and ZSM-5.

U.S. Pat. No. 3,945,913, Brennan, Mar. 23, 1976 discloses the preparation of BTX from alkylaromatics having nice or more carbon atoms.

U.S. Pat. No. 4,060,568, Rodewald, Nov. 29, 1977 discloses the preparation of low molecular weight olefins and p-xylene from alcohols using ZSM-5.

U.S. Pat. No. 4,097,367, Haag, June 27, 1978 discloses the preparation of BTX from olefinic naphthas and pyrolysis gasoline using ZSM-5.

U.S. Pat. No. 4,120,910, Chu, Oct. 17, 1978 discloses the preparation of $C_5{}^+$ aromatics and BTX by aromatizing ethane.

U.S. Pat. No. 4,157,293, Plank, June 5, 1979 discloses a method for preventing the loss of zinc from Zn-ZSM-5 during the preparation of BTX from $C_2$ to $C_{10}$ paraffins and olefins.

A survey of the background art shows a failure to recognize the process of the present invention. The benzene content of the BTX products is typically much less than 50%.

TECHNICAL DISCLOSURE

Our invention is embodied in a process for selectively preparing a product having a substantial benzene content from normal and slightly branched chain hydrocarbons, comprising:

(a) contacting a hydrocarbonaceous feed, which comprises normal and slighly branched chain hydrocarbons and has a boiling range above about 40° C. and below about 200° C. with a conversion catalyst which comprises an intermediate bore size zeolite and a Group VIII metal compound, and wherein said zeolite is substantially free of acidity; and (b) recovering a benzene containing effluent.

Feeds appropriate for use in the process contain normal and slightly branched alkanes or olefins, or both. The feeds can also contain naphthenes. Because the intermediate pore size zeolites used in the process are shape selective, the efficiency of the conversion will be greater the higher the proportion in the feed of molecules which can fit within or partially within the zeolites. Typical hydrocarbonaceous feedstocks appropriate for use have a boiling range of above about 40° C. and below about 200° C., preferably above about 60° C. and below about 120° C. Normal feeds for refinery production of benzene include light straight-run fractions and light naphthas. Paraffinic feeds, which are not efficiently dehydrocyclized by traditional reforming processes, can be efficiently processed using our invention. Whatever the feed source, the higher the proportion of $C_6$ and higher alkanes and olefins in the feed, the greater the efficiency of the process, and the higher the benzene content of the effluent. The most preferred feeds consist essentially of hydrocarbons having from 6 to 8 carbon atoms.

A particularly useful application of the present process is in upgrading the effluent produced by reforming. In typical reforming processes operating on typical reforming feeds, the n-paraffins are unconverted. By using the reformer effluent as the feed in our process for producing benzene, the aromatics content of the final reformate product can be substantially increased; the octane rating of the product increases as low octane n-paraffins are converted into high octane benzene.

The intermediate pore size zeolites used in the process are crystalline aluminosilicate zeolites having a silica to alumina mole ratio greater than about 10:1 and preferably greater than about 40:1. These zeolites have useful activity even at high silica:alumina mole ratios such as 1000 to 2000:1.

By "intermediate pore size" as used herein is meant an effective pore aperature in the range of about 5 to 6.5 Anstroms when the zeolite is in the H-form. Zeolites having pore apertures in this range tend to have unique molecular sieving characteristics. Unlike small pore zeolites such as erionite, they will allow hydrocarbons having some branching into the zeolitic void spaces. Unlike large pore zeolites such as the faujasties, they can differentiate between n-alkanes and slightly branched alkanes on the one hand and larger branched alkanes having, for example, quarternary carbon atoms.

The effective pore size of the zeolites can be measured using standard adsorption techniques and hydrocarbonaceous compounds of known minimum kinetic diameters. See Breck, *Zeolite Molecular Sieves*, 1974 (especially Chapter 8) and Anderson et al., J. Catalysis 58, 114 (1979), both of which are incorporated by reference.

Intermediate pore size zeolites in the H-form will typically admit molecules having kinetic diameters of 5 to 6 Anstroms with little hindrance. Examples of such compounds (and their kinetic diameters in Angstroms) are: n-hexane (4.3), 3-methylpentane (5.5), benzene (5.85), and toluene (5.8). Compounds having kinetic diameters of about 6 to 6.5 Angstroms can be admitted into the pores, depending on the particular zeolite, but do not penetrate as quickly and in some cases, are effecitvely excluded (for examle, 2,2-dimethylbutane is excluded from H-ZSM-5). Compounds having kinetic diameters in the range of 6 to 6.5 Angstroms include: cyclohexane (6.0), 2,3-dimethylbutane (6.1), 2,2-dimethylbutane (6.2), m-xylene (6.1) and 1,2,3,4-tetramethylbenzene (6.4). Generally, compounds having kinetic diameters of greater than about 6.5 Angstroms cannot penetrate the pore apertures and thus cannot be adsorbed in the interior of the zeolite. Examples of such larger compounds include: o-xylene (6.8), hexamethylbenzene (7.1), 1,3,5-trimethylbenzene (7.5), and tributylamine (8.1).

The preferred effective pore size range is from about 5.3 to about 6.2 Angstroms. ZSM-5, ZSM-11, and silicalite, for example, fall within this range.

In performing adsorption measurements to determine pore size, standard techniques are used. It is convenient to consider a particular molecular as excluded if it does not reach at least 95% of its equilibrium adsorption value on the zeolite in less than about 10 minutes (P/Po=0.5 25° C.).

Examples of intermediate pore size zeolites include silicalite and members of the ZSM series such as ZSM-5, ZSM-11, ZSM-12, ZSM-21, ZSM-23, ZSM-35, and ZSM-38.

ZSM-5 is described in U.S. Pat. Nos. 3,702,886 and 3,770,614; ZSM-11 is described in U.S. Pat. No. 3,709,979; ZSM-12 is described in U.S. Pat. No. 3,832,449; ZSM-21 is described in U.S. Pat. No. 3,948,758; and silicalite is described in U.S. Pat. No. 4,061,724. These patents are incorporated herein by reference. The preferred zeolites are silicalite, ZSM-5, and ZSM-11.

The conversion catalyst must include a Group VIII metal compound to have sufficient activity for commercial use. By Group VIII metal compound as used herein is meant the metal itself or a compound thereof. The Group VIII noble metals and their compounds, platinum, palladium, and iridium, or combinations thereof can be used. The most preferred metal is platinum. The Group VIII metal component can be impregnated into the zeolite after it is formed, or the metal can be included in the reaction mixture from which the zeolite is hydrothermally crystallized. It is highly desirable for the metal component to be dispersed uniformly throughout the zeolite, by inclusion in the hydrothermal crystallization mixture for example. The Amount of Group VIII metal present in the conversion catalyst should be within the normal range of use in reforming catalysts, from about 0.1 to 1.0 weight percent, preferably 0.2 to 0.8 weight percent, and most preferably 0.2 to 0.6 weight percent.

Reforming catalysts containing platinum are usually subjected to halogen or halide treatments to achieve or maintain a uniform metal dispersion and they also contain a halide component (especially a chlorine compound). The catalysts of our invention can be subjected to similar treatments without lessening the catalytic specificity for benzene synthesis. The halide treatment does not appear to have a significant effect on the yield of benzene.

The intermediate pore size zeolite/Group VIII metal conversion catalyst can be used without a binder or matrix. The preferred inorganic matrix, where one is used, is a silica-based binder such as Cab-O-Sil or Ludox. Other matrices such as magnesia and titania can be used. The preferred inorganic matrix is nonacidic.

It is critical to the selective production of benzene in useful quantities that the conversion catalyst be substantially free of acidity, for example by poisoning the zeolite with a basic metal, e.g., alkali metal, compound. Intermediate pore size zeolites are usually prepared from mixtures containing alkali metal hydroxides and thus have alkali metal contents of about 1-2 weight percent. These high levels of alkali metal, usually sodium or potassium, are unacceptable for most catalytic applications because they cause a high fouling rate. Usually, the alkali metal is removed to low levels by ion-exchange with hydrogen or ammonium ions. By alkali metal compound as used herein is meant elemental or ionic alkali metals or their basic compounds. Surprisingly, unless the zeolite itself is substantially free of acidity, the basic compound is required in the present process to direct the synthetic reactions to benzene production.

The amount of alkali metal necessary to render the zeolite substantially free of acidity can be calculated using standard techniques based on the aluminum content of the zeolite. Under normal circumstances, the zeolite as prepared and without ion-exchange will contain sufficient alkali metal to neutralize the acidity of the catalyst. If a zeolite free of alkali metal is the starting material, alkali metal ions can be ion exchanged into the zeolite to substantially eliminate the acidity of the zeolite. An alkali metal content of about 100%, or greater, of the acid sites calculated on a molar basis is sufficient.

Where the basic metal content is less than 100% of the acid sites on a molar basis, the following test can be used to determine if the zeolite is substantially free of acidity. The test procedure is as follows: 0.1-0.5 g of catalyst is mixed with 1g of acid-washed and neutralized alundum and packed in a 3/16" stainless steel reactor tube with the remaining space filled with alundum. The reactor contents are calcined for one hour at 450° C. The reactor is then placed in a clam-shell furnace and the reactor outlet connected to the inlet of a gas chromatograph. The inlet is connected to the carrier gas line of the GC. Helium is passed through the system at 30 cc/min. 0.04 Microliter pulses of n-decane are injected through a septum above the reactor and reaction products are determined by standard GC analysis. Blank runs with alundum should show no conversion under the experimental conditions, nor should a 100% Catapal alumina catalyst.

A pseudo-first-order, cracking rate constant, k, is calculated using the formula $$k = \frac{1}{A} \ln \frac{1}{1-x}$$

where A is the weight of zeolite in grams and x is the fractional conversion to products boiling below decane. The zeolite is substantially free of acidity when the value for ln k is less than about $-3.8$.

The preferred alkali metals are sodium and potassium. The zeolite itself can be substantially free of acidity only at very high silica:alumina mol ratios; by "zeolite consisting essentially of silica" is meant a zeolite which is substantially free of acidity without base poisoning.

The reaction conditions for the process typically include pressures ranging from atmospheric to 10 bar, and liquid hourly space velocities (LHSV) ranging from 0.1 to 15. If desired, hydrogen can be mixed with the feed to lessen the tendency of the catalyst to foul, but hydrogen need not be used. The reactions can take place at temperatures above 480° C. Surprisingly, the process is most efficient at relatively high temperatures, above 510° C. and ranging up to about 595° C.

By substantial amount of benzene is meant a benzene content of the $C_5+$ aromatics produced which is greater than about 50% by weight of the $C_5+$ aromatics, preferably greater than about 60% by weight, and most preferably greater than about 75% by weight.

The following examples illustrate the invention. All percentages given are by weight, unless otherwise indicated.

Two light straight-run feeds were used in the tests.

| Feed 1 | |
|---|---|
| Gravity, °API | 79 |
| Nitrogen, ppm | <0.1 |
| Sulfur, ppm | <0.2 |
| Vol. % paraffin | 83.6 |
| Distillation (D86) °F.: | |
| Start/5 | 118/123 |
| 10/30 | 126/135 |
| 50 | 143 |
| 70/90 | 156/177 |
| 95/EP | 194/297 |
| Feed 2 | |
| Gravity, °API | 75 |
| Nitrogen, ppm | <0.1 |
| Sulfur, ppm | <0.02 |
| Vol. % paraffin | 77.2 |
| Distillation (D86) °F.: | |
| Start/5 | 120/133 |
| 10/30 | 136/147 |
| 50 | 157 |
| 70/90 | 170/198 |
| 95/EP | 216/254 |

EXAMPLE 1

A series of experiments were performed to illustrate the necessity of using a zeolite substantially free of acidity to produce benzene. In the first set of experiments a zeolite prepared according to U.S. Pat. No. 4,061,724 and having a silica:alumina mole ratio of 892:1 was used. No inorganic matrix was used. Feed 2 was used as were the following conditions: LHSV=1, no hydrogen, 3.4 bar (gauge), and 538° C. Calculations show that 0.16% sodium would saturate the acid (aluminum) sites.

| | A | B | C |
|---|---|---|---|
| Catalyst | | | |
| Na level, % | 0.017 | 0.99 | 4.12 |
| Pt level, % | 0.33 | 0.38 | 0.44 |
| Product | | | |
| $C_5+$, % of feed | 36.88 | 79.69 | 85.59 |
| Aromatics, % of $C_5+$ | 91.60 | 66.43 | 42.57 |
| Benzene, % of aromatics | 8.81 | 65.45 | 65.89 |

These data show that as the sodium level increased (as the acidity of the zeolite decreased and was neutralized) the yield of the $C_5+$ fraction increased and the benzene content of the $C_5+$ aromatics fraction increased substantially.

A second set of experiments also showed the surprising effect of an acid-free zeolite on benzene specificity. Again using Feed 2, LHSV=1, $H_2/HC$=1, 1.65 bar (gauge), and 538° C. together with zeolites exhibiting the ZSM-5 X-ray diffraction pattern and having a silica:alumina mole ratio of 121:1 (D and E), and, prepared according to U.S. Pat. No. 4,061,724 (F; silica:alumina mol ratio of 938:1), the following results were obtained:

| | D | E | F |
|---|---|---|---|
| Catalyst | | | |
| Na level % | 2.03 | 0.005 | 1.14 |
| Pt % | 0.44 | 0.34 | 0.36 |
| Re % | 0.42 | 0.37 | 0 |
| Cl % | 0.49 | <0.05 | 0 |
| Product | | | |
| $C_5+$, % of feed | 52.67 | 37.54 | 48.55 |
| Aromatics, % of $C_5+$ | 88.63 | 92.05 | 92.82 |
| Benzene, % of Aromatics | 89.14 | 34.12 | 94.76 |

These data also illustrate the significant selectivity towards benzene production of the present invention.

Further experiments to show the selective production of benzene in the aromatics fraction and the effect of alkali metal poisoning were performed using a zeolite prepared according to U.S. Pat. No. 4,073,865, Flanigen, Feb. 14, 1978 and having an aluminum content of 950 ppm (W/W). The reactions were performed on Feed 2 at LHSV=1, no hydrogen, 3.3 bar (gauge), and 538° C.

| | G | H |
|---|---|---|
| Catalyst | | |
| Na % | 2.82 | <0.005 |
| Pt % | 0.49 | 0.24 |
| Product | | |
| $C_5+$ % of feed | 83.55 | 43.61 |
| Aromatics % of $C_5+$ | 15.47 | 63.43 |
| Benzene, % of aromatics | 62.44 | 7.91 |

Although the aromatics fraction of the $C_5+$ product of G is low, it has a high benzene content, and, based on feed converted, G produced significantly more benzene (ca. 8%) than H (ca. 2.5%).

EXAMPLE 2

Experiments were performed to show the necessity of having a Group VIII metal present to achieve not only benzene selectivity but also reasonable yields of aromatics. Feed 2 was used along with LHSV=1, 3.3 bar (gauge), no hydrogen, and 538° C. The zeolites of I exhibited the X-ray diffraction pattern of ZSM-5 while the zeolite of J was prepared according to U.S. Pat. No. 4,061,724. The zeolites were not composited with an inorganic matrix.

|  | I | J |
|---|---|---|
| Catalyst |  |  |
| SiO$_2$:Al$_2$O$_3$ | 67.4 | 892 |
| Na % | 1.02 | 0.99 |
| Pt % | 0 | 0.38 |
| Product |  |  |
| C$_5^+$, % of feed | 95.64 | 79.69 |
| Aromatics, % of C$_5^+$ | 3.24 | 66.43 |
| Benzene, % aromatics | 49.69 | 65.45 |

These data show that the Group VIII metal, platinum in this case, is necessary not only to yield a high benzene fraction of the aromatics formed, but also to yield practical amounts of an aromatic fraction.

EXAMPLE 3

The preceding examples show that benzene can be selectively produced in high yields from zeolites having a wide range of silica:alumina mole ratios. Several further experiments were also performed to illustrate this activity. The catalyst of K was prepared according to U.S. Pat. No. 4,061,724 while that of L exhibited the ZSM-5 X-ray diffraction pattern. Reaction conditions included 1.65 bar (gauge), H$_2$/HC=1, LHSV=1, and 538° C.

|  | Feed | |
|---|---|---|
|  | #1 K | #2 L |
| Catalyst |  |  |
| Silica:Alumina | 938 | 121 |
| Na % | 1.14 | 2.03 |
| Pt % | 0.35 | 0.44 |
| Re % | 0.54 | 0.42 |
| Cl % | 0.75 | 0.49 |
| Product |  |  |
| C$_5^+$, % of feed | 47.43 | 52.67 |
| Aromatics, % of C$_5^+$ | 100 | 88.63 |
| Benzene, % of aromatics | 87.73 | 89.14 |

EXAMPLE 4

Feed #2 was processed with a platinum (0.36%), sodium (1.14%) zeolite prepared according to U.S. Pat. No. 4,061,724 and having a silica:alumina mole ratio of 938:1. The reaction conditions included LHSV=1, 1.65 bar (gauge), H$_2$/HC=1, and 538° C. The products were compared at the beginning and end of the run.

|  | Beginning (after 1 hour) | End (after 20 hours) |
|---|---|---|
| C$_5^+$, % of feed | 57.63 | 80.48 |
| Aromatics, % of C$_5^+$ | 87.30 | 57.78 |
| Benzene, % of aromatics | 85.2 | 75.2 |
| % of feed | 42.86 | 35.89 |
| C$_7^+$ aromatics, % of feed | 7.45 | 11.60 |
| Unconverted feed | 7.05 | 33.97 |

These data illustrate the surprising result, that as the catalyst fouls, the yield of C$_5^+$ increases, benzene remains a major component of the C$_5^+$ aromatics, benzene remains a major product, and non-benzene aromatics remain a minor portion of the product. The sites which have undesirable cracking activity foul faster than the benzene synthesis sites.

EXAMPLE 5

According to the dehydrocyclization mechanism through which conventional reforming proceeds, an n-heptane feed would yield a product which is primarily toluene, with only small amounts of benzene and other aromatics. An experiment was performed using an n-heptane feed, a platinum, sodium ZSM-5 zeolite and LHSV=1, 1.65 bar (gauge), H$_2$/HC=1, and 538° C. The data from the beginning and end of the experiment show significant amounts of benzene are produced from n-heptane.

|  | Beginning (after 1 hour) | End (after 20 hours) |
|---|---|---|
| C$_5^+$, % of feed | 58.98 | 69.26 |
| Aromatics, % of C$_5^+$ | 94.87 | 84.32 |
| Benzene, % of feed | 39.40 | 21.99 |
| C$_7^+$ aromatics % of feed | 16.56 | 36.41 |
| Unconverted feed | 1.92 | 3.65 |

EXAMPLE 6

An experiment was performed using Feed #2 and a zeolite exhibiting the ZSM-5 X-ray diffraction pattern. The alkali metals were sodium (in M) and potassium (in N). Reaction conditions included 3.3 bar (gauge), no hydrogen, LHSV=1, and 538° C.

| Catalyst | M | N |
|---|---|---|
| Cation level, % | 0.99 | 1.46 |
| Pt, % | 0.38 | 0.34 |
| C$_5^+$, % of feed | 79.69 | 68.59 |
| Aromatics, % of C$_5^+$ | 66.43 | 40.08 |
| Benzene, % of aromatics | 65.45 | 76.67 |
| Closure | 98.77 | 89.50 |

These data indicate that an aromatics fraction with a high benzene content can be prepared from a zeolite whose acidity is neutralized by different alkali metals.

EXAMPLE 7

An experiment was performed using Feed #1 and a zeolite prepared according to U.S. Pat. No. 4,061,724 to show the effect of halide on the content of the C$_1$ and C$_4$ gas. The catalysts were unbound.

|  | O | P |
|---|---|---|
| Catalyst |  |  |
| Cl, % | 0.75 | 0 |
| Pt, % | 0.35 | 0.48 |
| Re, % | 0.54 | 0.70 |
| Na, % | 1.14 | 1.14 |
| Product Yield |  |  |
| C$_5^+$, % | 47.43 | 70.18 |
| Aromatics, % of C$_5^+$ | 100 | 52.22 |
| Benzene, % of C$_5^+$ aromatics | 87.73 | 77.10 |
| Methane, wt % of feed | 55.62 | 11.98 |
| C$_2$ | 0 | 4.97 |
| C$_3$ | 0 | 5.35 |
| C$_4$ | 0 | 7.24 |

The test shows the selective production of methane as opposed to the other light gases.

What is claimed is:

1. A process for selectively preparing a product having a substantial benzene content from normal and slightly branched hydrocarbons, comprising
   (a) contacting a hydrocarbonaceous feed, which comprises normal and slightly branched hydrocarbons and has a boiling range above about 40° C. and less than about 200° C. with a conversion catalyst which comprises an intermediate pore size zeolite and a platinum compound, and wherein said zeolite is substantially free of acidity; and
   (b) recovering a benzene containing effluent.

2. A process according to claim 1 wherein intermediate pore size zeolite has pore apertures in the range of about 5 Angstroms to about 6.5 Angstroms.

3. A process according to claim 1 wherein said zeolite is selected from ZSM-5, ZSM-11, and silicalite.

4. A process according to claim 1 wherein said zeolite contains a sufficient quantity of an alkali metal compound to be substantially free of acidity.

5. A process according to claim 4 wherein said zeolite has an alkali metal content of about 100%, or greater, of the acid sites in said zeolite on a molar basis.

6. A process according to claim 5 wherein said alkali metal is selected from potassium and sodium.

7. A process according to claim 1 wherein said zeolite consists essentially of silica.

8. A process according to claim 1 wherein said feed has a boiling range above about 60° C. and below about 120° C.

9. A process according to claim 8 wherein said feed consists essentially of hydrocarbons having from 6 to 8 carbon atoms.

10. A process according to claim 1 wherein said contacting occurs at a temperature above about 480° C.

11. A process according to claim 10 wherein said contacting occurs at a temperature above about 510° C.

12. A process according to claim 10 wherein said conversion catalyst further comprises a halide component.

13. A reformer effluent upgrading process, comprising:
   (a) reforming a reformer feed to produce a reformer effluent; and
   (b) producing an upgraded reformate having an increased benzene concentration by contacting said reformer effluent with a conversion catalyst which comprises an intermediate pore size zeolite and a platinum compound, and wherein said zeolite is substantially free of acidity.

* * * * *

UNITED STATES PATENT AND TRADEMARK OFFICE
CERTIFICATE OF CORRECTION

PATENT NO. : 4,347,394
DATED : August 31, 1982
INVENTOR(S) : Clifford M. Detz and Leslie A. Field It is certified that error appears in the above-identified patent and that said Letters Patent are hereby corrected as shown below:

Col. 1, line 44, "number U.S." should read --number of U.S.--.

Col. 1, line 68, "nice or" should read --nine or--.

Col. 3, line 3, "6,5 Anstroms" should read --6.5 Angstroms--.

Col. 3, line 21, "6 Anstroms" should read --6 Angstroms--.

Col. 3, line 28, "examle" should read --example--.

Col. 3, line 45, "molecular" should read --molecule--.

Col. 8, line 51, "$C_1$ and $C_4$" should read --$C_1$ to $C_4$--.

Claim 12, Col. 10, line 1, "according to claim 10" should read --according to Claim 1--.

Signed and Sealed this

Fourth Day of January 1983

[SEAL]

Attest:

Attesting Officer

GERALD J. MOSSINGHOFF

Commissioner of Patents and Trademarks